United States Patent [19]

Faccioli et al.

[11] Patent Number: 5,728,096
[45] Date of Patent: Mar. 17, 1998

[54] EXTERNAL TROCHANTER SPLINT

[75] Inventors: Giovanni Faccioli, Monzambano; Lodovico Renzi Brivio; Franco Lavini, both of Verona; Daniele Venturini, Povegliano Veronese, all of Italy

[73] Assignee: Orthofix S.r.l., Bussolengo, Italy

[21] Appl. No.: 766,086

[22] Filed: Dec. 16, 1996

Related U.S. Application Data

[63] Continuation of Ser. No. 517,847, Aug. 22, 1995, abandoned.

[30] Foreign Application Priority Data

Aug. 23, 1994 [IT] Italy ................................ VR94A0075

[51] Int. Cl.$^6$ ............................................ A61B 17/56
[52] U.S. Cl. ............................................ 606/54; 606/59
[58] Field of Search ........................... 606/54, 55, 57, 606/58, 59, 65, 66, 67, 68

[56] References Cited

U.S. PATENT DOCUMENTS

| | | | |
|---|---|---|---|
| 5,160,335 | 11/1992 | Wagenknecht | 606/59 |
| 5,207,676 | 5/1993 | Canadell | 606/54 |
| 5,209,750 | 5/1993 | Stef | 606/59 |
| 5,320,622 | 6/1994 | Faccioli et al. | 606/58 |
| 5,429,637 | 7/1995 | Hardy | 606/54 |

Primary Examiner—Michael Buiz
Assistant Examiner—Daphna Shai
Attorney, Agent, or Firm—Hopgood, Calimafde, Kalil & Judlowe

[57] ABSTRACT

An external trochanter splint, especially for surgical stabilization of femoral pertrochanter and subtrochanter fractures, comprises a pair of clamps (2,3) each with its own longitudinal axis (a,b). One of these clamps (2) is designed for the movable locking of a first group of bone screws or bolts (V) inserted into the mass of the trochanter, the other (3) is designed for the movable locking of a second group of bone screws or bolts (W) inserted into the proximal diaphysis of the femur. The two clamps are connected together in side-by-side relation via an intermediate connecting member (4). First provision is made for immobilizing a selected angle of divergence ($\alpha$) between the longitudinal axes (a,b) and second provision is made for immobilizing a selected angle of rotation of at least one of the said clamps (3) about its own longitudinal axis (b). Intermediate member (4) comprises a central body (21) connected to clamps (2,3) via a pair of rotatable joints with corresponding axes of rotation (c,d) which are substantially at right angles. In alternative embodiments, the bone screws or bolts of the clamp along the trochanter can be immobilized along convergent alignments; the joint between the two clamps has one or more frustoconical contact surfaces; and the clamp to the femur is subdivided into two parts which can be angularly oriented about the longitudinal axis of the clamp.

31 Claims, 6 Drawing Sheets

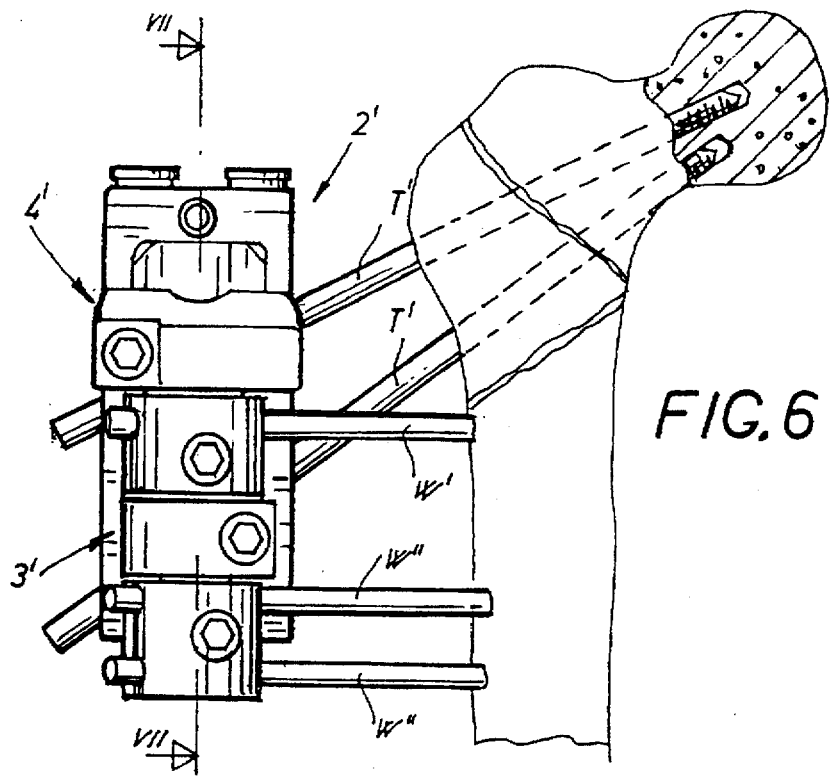
FIG. 6
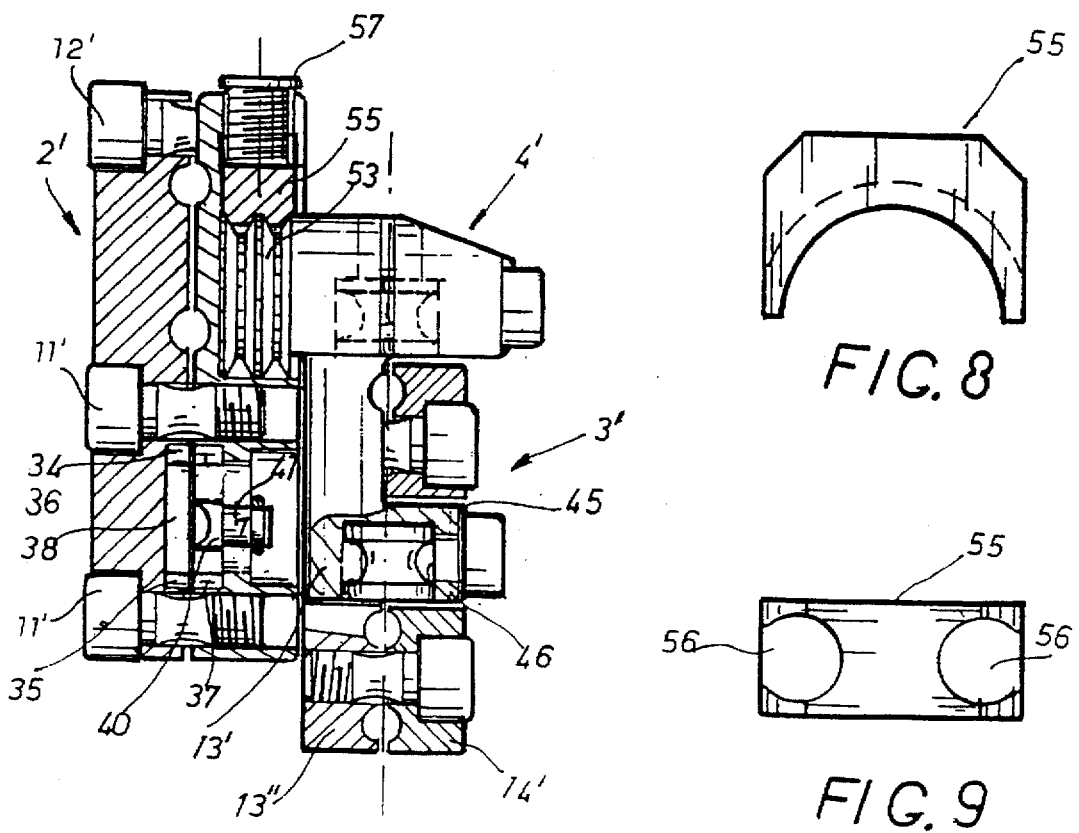
FIG. 7
FIG. 8
FIG. 9

EXTERNAL TROCHANTER SPLINT

RELATED CASE

This application is a continuation of original application Ser. No. 08/517,847, filed Aug. 22, 1995 now abandoned.

BACKGROUND OF THE INVENTION

This invention relates to an external trochanter splint, particularly for the stabilization of pertrochanter and subtrochanter fractures by means of groups of bone screws inserted into the outer proximal third of the femur.

It is known that pertrochanter and persubtrochanter fractures are fractures of the proximal third of the femur which are by nature unstable and in which bone regrowth is difficult. These fractures are frequent in patients of medium to advanced age, who are normally subject to appreciable rarefaction of the metaphysis region due to osteoporosis, and may occur in victims of high energy impacts suffering from multiple injuries.

A known technique for stabilizing trochanter fractures provides for the use of internal splint devices, i.e. those which are held within the limb until the fragments have become completely solid, such as endomedullary bolts, sheet-plate assemblies and screw-plate assemblies.

An alternative technique provides for the use of external stabilization devices, i.e. those designed to be held partly outside the limb over the patient's skin; such devices generally include two groups of bone screws which are located respectively in a proximal position close to the neck of the femur and in a distal position close to the knee. These two groups are rigidly secured together by an external structure or frame.

This invention relates to devices of the latter type.

One of the major disadvantages of external splints lies in the fact that the group of distal screws is so close to the knee that it limits its flexion, causing excessive stress on the tendon part of the tensor of the fascia lata with consequent accentuated pain in the muscle. This results in a stiffening of the joint, which requires greater time and cost in order to recover mobility of the limb and rehabilitative physiotherapy.

A further disadvantage lies in the appreciable loss of blood associated with the implantation of the bone screws in the vicinity of the tensor muscle.

Another disadvantage lies in the frequent need for further surgical intervention to remove conventional splints, on account of their relative complexity.

BRIEF STATEMENT OF THE INVENTION

The invention is designed to overcome the above-mentioned disadvantages through a reliable compact, comfortable and economic external trochanter splint.

A particular object is to provide an extremely compact trochanter splint which can be easily positioned by the surgeon.

Another object is to provide an external splint which eliminates interaction with the tendon part of the fascia lata, thus permitting absolute mobility of the knee without any pain in the joint, in order to effect a drastic reduction in the time and cost of post-operative recovery.

A further object is to provide a trochanter splint which involves less vascularized areas and muscular tissues, in order to reduce blood loss during the operation.

A further object also consists of simplifying the device with the view to permitting the splint to be removed on an out-patient basis without any complex operation in the operating theater.

The invention accomplishes these objects through an external trochanter splint, particularly for the surgical stabilization of femoral pertrochanter and subtrochanter fractures. The splint comprises a pair of clamps each of which has its own longitudinal axis; one of these clamps is adapted to immobilize a first group of bone screws inserted into the mass of the trochanter, and the other is adapted to immobilize a second group of bone screws in the proximal diaphysis of the femur. An intermediate member connects the respective clamps to each other in an approximately side-by-side relation. The connection of the clamps to the intermediate member is such as to permit a first selective rotary adjustment and immobilization of a desired angle of divergence between the said longitudinal axes, and also to permit a second selective rotary adjustment and immobilization of at least one of the said clamps about its own longitudinal axis.

Preferably, the intermediate member is connected to the clamps by means of a pair of rotatable joints, which respectively have fixed axes of rotation that are in substantially a right angle relation.

Each joint may include a cylindrical seat or bearing on one side, and a stud or pin of a complementary shape rotatably housed in the said seat on the other side.

The body of the intermediate member has a central bore or through-hole which forms a seat or bearing for a first rotary joint. It also has an external lateral formation which projects substantially perpendicular to the axis of the central bore or through-hole, defining a pin or stud for a second rotary joint.

In a preferred embodiment, one of the clamps is a trochanter clamp having means to immobilize trochanter screws with converging axes, and the other clamp is a diaphysis or femur clamp that is subdivided into two parts which can be mutually rotated about the longitudinal axis of the clamp to offset two groups of femoral screws at an angle to each other.

In addition, the first rotary joint has co-acting contact means comprising one or more surfaces of frustoconical shape.

The external trochanter splint according to the invention provides appreciable stability for a fracture to be joined and increases the comfort of the patient, who can move freely immediately after the operation, reducing recovery times and hospital stays, with an appreciable benefit in economic terms.

In addition to this, the splint is adapted for location in areas relatively remote from highly vascularized muscular tissues, thus reducing blood loss in surgical installation.

The relative structural simplicity of the splint makes it possible to remove it on an out-patient basis, thus avoiding any need to return to the operating theater. Finally, in the case of a complex or labile fracture, the possibility of orienting both the trochanter screws and the diaphysis or femur screws of the respective clamps enormously increases the adaptability of the splint and its stability after installation.

BRIEF DESCRIPTION OF THE DRAWINGS

Further features and advantages of the invention will become apparent from the accompanying detailed description of several preferred embodiments, in conjunction with the accompanying drawings in which:

FIG. 6 is a side view of an alternative embodiment of the invention, in application to a relatively labile persubtrochanter fracture affecting the neck of the femur;

FIG. 7 is a front view of the splint of FIG. 6, in partial section in a plane along the line VII—VII of FIG. 6;

FIG. 8 is a front view of a component part of the external splint of FIG. 6;

FIG. 9 is a view from above the component part of FIG. 8;

DETAILED DESCRIPTION

Figure 1:
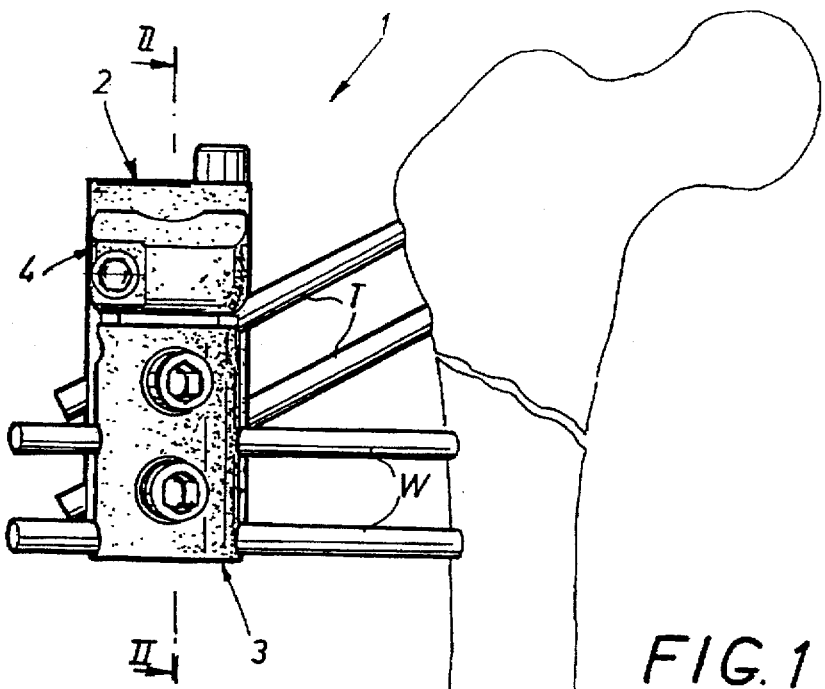
FIG. 1 is a side view in elevation of an external trochanter splint of the invention applied to a subtrochanter femoral fracture.
Figure 2:
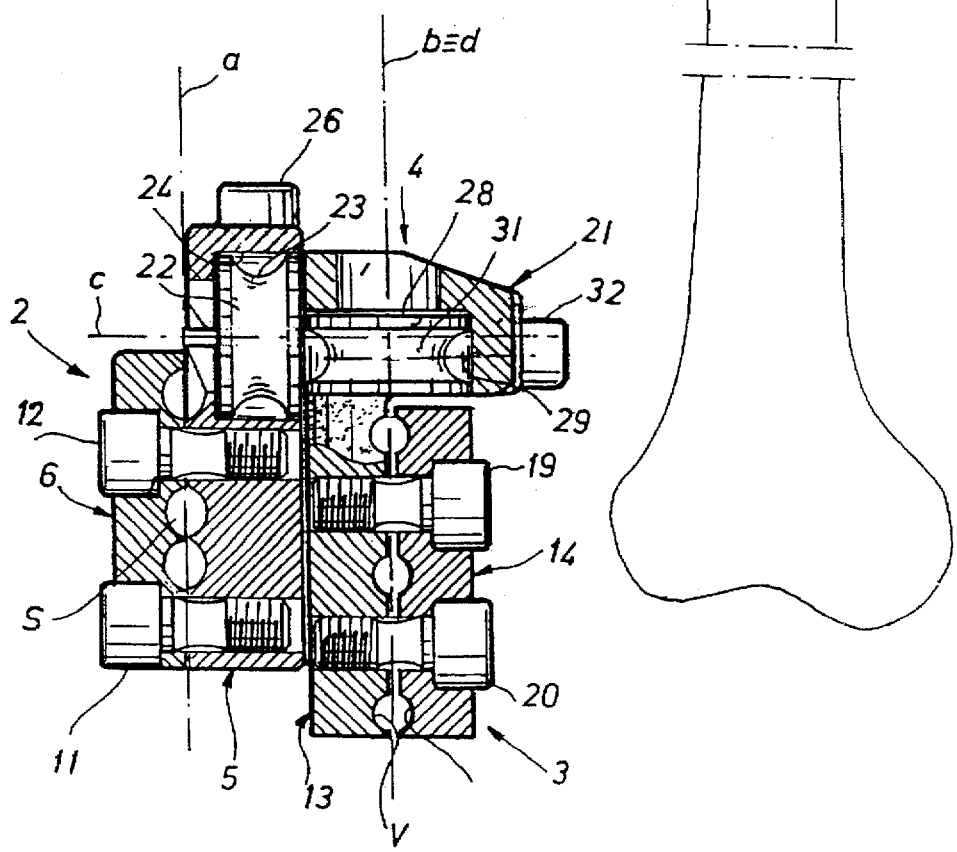
FIG. 2 is a sectional view of the external splint of FIG. 1, taken substantially in the plane II—II of FIG. 1.
Figure 3:
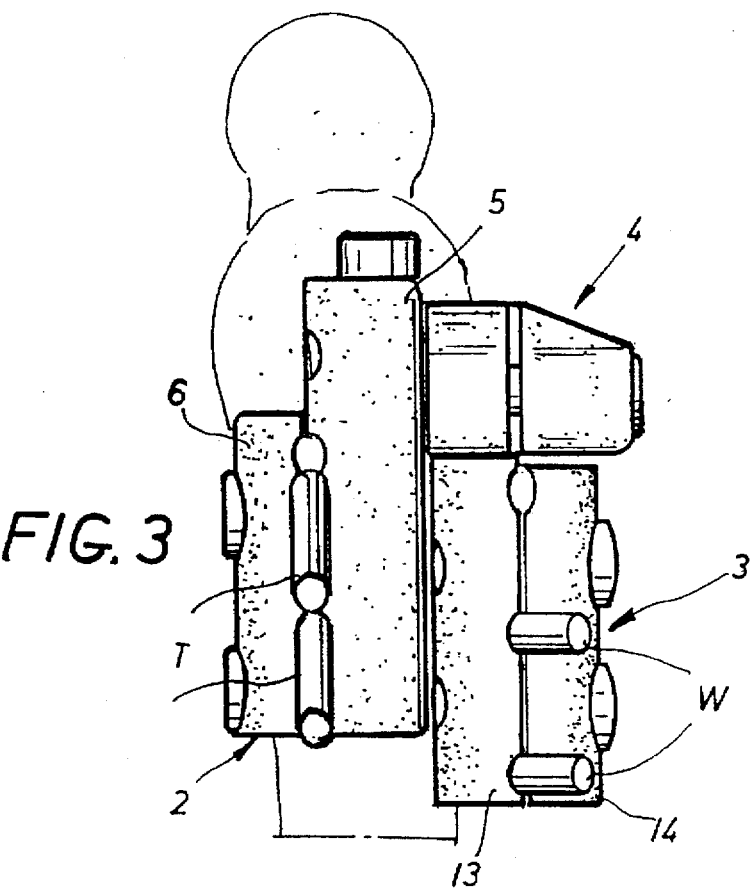
FIG. 3 is a front view of the external splint of FIG. 1.
Figure 4:
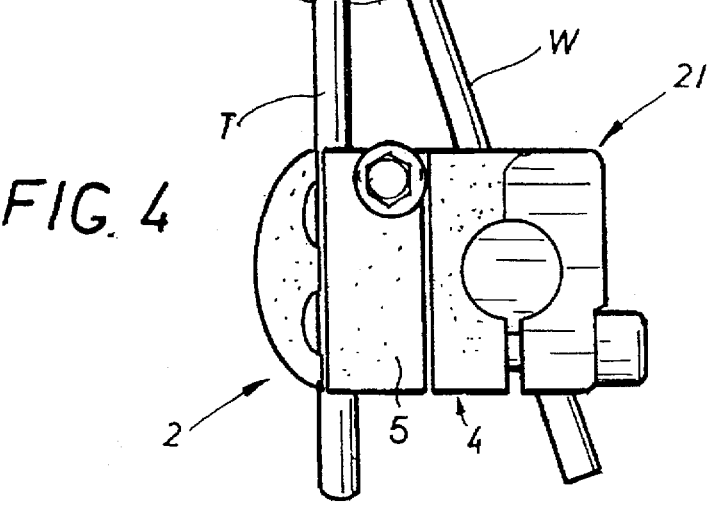
FIG. 4 is a view from above of the external splint of FIG. 1.

In the drawings, a trochanter splint of the invention is indicated as a whole by reference numeral 1, and is seen to comprise a pair of clamps 2, 3 connected by an intermediate member 4.

Each clamp comprises two mutually confronting members, a base and a cover respectively, which can be coupled together by suitable tightening means.

In particular, a first or trochanter clamp 2 comprises a base 5 and a cover 6 which have confronting internal faces which are substantially flat. In the illustrated embodiment, base 5 is of generally rectangular prismatic shape, with an external face which is also flat, while the cover has a rounded generally cylindrically arcuate external face, to avoid edges and to harmonize with the limb. The two members 5, 6 have pairs of aligned bores or through-holes, namely, a pair of smooth bores 7, 8 in cover 6 and a pair of threaded bores 9, 10 in base member 5, for recessed-head (e.g., Allen-head) locking bolts 11, 12.

Once joined together, the two members 5, 6 define a longitudinal axis a for clamp 2 resulting from the intersection of a plane separating the flat confronting faces of the members with a plane perpendicular to these faces and passing through the middle thereof, e.g., as defined by the axes of the locking bolts 11, 12.

On the internal faces of the two members 5, 6, a first set of opposed transversely grooved seats R is provided in spaced substantially parallel relation. Seats R are inclined with respect to axis a at an angle α approximately equal to that of the mean inclination of the neck of the trochanter with respect to the axis of the femur. Provision may be made in each member 5, 6 for a second set of seats S which are symmetrical but at opposite inclination with the first set, with reference to the mid line of the confronting internal faces in order to permit fitting to either a right limb or a left limb.

By tightening bolts 11, 12 and members 5, 6 it is possible to stably immobilize a set of bone screws T, previously located in the mass of the trochanter, so that they pass partly through the neck and the head of the femur. For this reason, clamp 2 is referred to hereinafter merely as the trochanter clamp. It will be noted that, once tightened, a very small space remains between the two members and this reduces the problem of differentiated immobilization of the bolts which can occur when one bolt is tightened before another.

In similar fashion, the second clamp 3 comprises a base 13 and a cover 14, both having substantially flat confronting internal faces and rounded external faces, so as generally to have the shape of half cylinders. In this case again, members 13, 14 have through-holes, namely, smooth bores 15, 16 in cover 14 and threaded bores 17, 18 in base 13 respectively, to house recessed-head locking bolts 19, 20. Once members 13, 14 are joined together, the clamp 3 has a longitudinal axis b defined as previously indicated for clamp 2.

On the internal faces of members 13, 14, a first set of opposed transversely grooved seats V is provided. In this case, seats V are substantially perpendicular to the longitudinal clamp axis b, in that they are designed to stably immobilize a series of bone screws W previously inserted in the proximal diaphysis of the femur. For this reason, clamp 3 is referred to hereinafter as the diaphysis or femur clamp. It will be noted that these screws W have the advantage of being located in a position sufficiently distant from the tendon part of the fascia lata so as to avoid pain and to avoid such limitation of knee-joint action as is typical of conventional external trochanter splints.

Intermediate member 4 couples the two clamps 2, 3 in side-by-side relation and selectively determines their relative orientation by means of their respective rotary joints.

In the form shown, intermediate member 4 has a body 21 of approximately rectangular prismatic shape, defining two mutually perpendicular axes c and d, respectively. Body 21 includes an extension 22 of approximately cylindrical shape about axis c and with a peripheral groove 23. Extension 22 defines a stud or pin which has journalled support in a corresponding seat or bore 24 in base 5, so as to define a first rotary coupling joint. Seat 24 yields elastically in that base 5 has a radial notch or slit 25 in a region of minimum thickness. A securing bolt 26 can be inserted into a partly threaded bore 27 in base 5. Insertion of bolt 26 in bore 27 after extension 22 of intermediate member 4 has been housed in seat 24 avoids involuntary detachment of the trochanter clamp 2 from intermediate member 4. Tightening bolt 26 immobilizes an adjusted angle of base 5, and therefore of the axis a of clamp 2, with respect to the axis d of intermediate member 4.

The second rotary joint is defined by an axial extension or stud formation 28 of base 13 of clamp 3; formation 28 is of a substantially cylindrical shape and can be inserted into an internal seating bore 29 of the body 21 of member 4, on axis d. Seat 29 can yield elastically owing to the presence of a radial slit 30 on its lateral wall, preferably in a region of minimum thickness. Again, axial extension 28, which defines the pin or stud of the second rotary joint, has a peripheral groove 31 for the passage of a bolt 32 inserted into a bore 33 which is partially threaded internally and provided in body 21 of member 4, serving to enclose seat 29 elastically. When bolt 32 is inserted into bore 33, the groove 31 of axial extension 28 is engaged, thereby retaining the diaphysis clamp 3 against separation from intermediate member 4.

In use, the surgeon inserts at least one pair of screws T into the mass of the trochanter and at least one pair of screws W into the proximal diaphysis zone of the femur, in suitable holes previously made in the bone through the use of a guide mask (not shown); alternatively, the said clamps may be used as drill guides.

After this, bolts 26 and 32 are backed off to release the rotary joints which connect intermediate connecting member 4 to clamps 2 and 3. Clamps 2, 3 are then oriented, varying the angle of divergence between their respective axes a, b and the angle of clamp 3 about its own axis b. Bolts 11, 12, 19, 20 are then tightened, immobilizing clamp members 2, 3 to their corresponding groups of bone screws T, W. At this point, the surgeon, using a brilliance emitter (image intensifier), can set the fracture in one or more X-ray exposure planes. Finally, bolts 26, 32 are tightened to stabilize the fracture.

The alternative embodiment of FIGS. 6 to 12 differs from that of FIGS. 1 to 5 in three special technical features affecting the two clamps and a joint between them. These differences are described below, using reference numbers with primed notation to identify details corresponding to those of FIGS. 1 to 5.

The first difference relates to the structure of trochanter clamp 2' and in particular its means for securing the trochanter screws. As in the previous embodiment, the clamp comprises a base 5' and a cover 6' which face each other and are secured by securing bolts 11', 12' with recessed hexagonal heads which pass through corresponding smooth bores 7', 8' provided in cover 6' and engage threaded bores 9', 10' provided in base 5'.

The upper part of the flat confronting faces of base 5' and cover 6' are seen to be provided with a first set of parallel fixed transverse grooves or seats R' inclined at an angle α with respect to the axis a' of the clamp to immobilize one or two bone screws which pass through the mass of the trochanter and part of the neck of the femur. And a second set of oppositely inclined grooves or seats S' is symmetrical with respect to seats R' so that the clamp can be used on either the left or right limb. It will be noted that these means for securing the trochanter screws are of the fixed type, for holding a parallel relation of bone screws.

It has been verified clinically that the screws which pass through the neck of the femur can slip if they are perfectly parallel, i.e. they can progressively penetrate the bone tissue as a result of the mechanical stresses acting on the femur, to the extent that their ends can even project from the head of the femur, immobilizing the joint.

One means of avoiding this disadvantage is to provide non-parallel screws, i.e. slightly converging screws, while keeping them in the same vertical plane. However, it is not easy to provide a precise suitable angle of convergence for every configuration and for every possible break in a femur.

For this reason, an angularly adjustable securing point has been provided, in addition to the upper fixed sets of grooves R', S'. To this end, the lower part of the inside flat face of cover 6' is shown with a butterfly-shaped slot or recess 50 leaving two projections 34, 35 with V-shaped sides provided with bores 7'. On the confronting face of base 5', an identical butterfly-shaped recess will be understood to define corresponding projections 36, 37 which, are mirror images of projections 34, 35. When the two members (5', 6') are coupled together, the said recesses a cavity 38 which is capable of housing a support 39 for a trochanter screw T". The support comprises a channel member 40 having a perpendicular pin 41 for guided engagement in an elongate slot 42 in base 5', with freedom to rotate and to slide vertically (i.e., longitudinally). After pin 41 has been inserted in slot 42, an elastomeric O-ring 43 is fitted on the end of pin 41, and is retained by the enlarged head (44) of pin 41 to retain the pin against loss in an axial direction. When bolts 11', 12' are tightened, screw T" is secured and is immobilized between support 39 and the opposite face of cover 6'. As a result of this arrangement, the surgeon can vary the angle of inclination δ formed between the lower trochanter screw T" and the axis of the clamp at will, so as to make this screw converge towards the other upper trochanter screw or screws T', thus avoiding the danger of breaking the femoral head.

The second modification relates to the diaphysis clamp, in particular its method of securing its corresponding bone screws W', W". From a practical point of view, some difficulties have been encountered with the insertion of these screws, especially the one furthest from the femoral head, namely difficulties which largely depend on the accuracy with which the screws have been inserted into the neck of the femur.

In order to reduce such difficulties, the diaphysis clamp has been modified so as to allow the distal diaphysis bone screws to be angularly oriented with respect to the proximal screws; to this end, a third lockable rotary joint is provided on an axis identical to that of the axis d' of clamp 3'.

More specifically, the diaphysis clamp 3' comprises an upper base member 13', generally in the shape of a half cylinder, and an upper cover 14' tightened by a bolt 19' to immobilize a first bone screw W' in opposing seats V'. The lower part of base member 13' has an enlarged formation 45 with an internal cylindrical cavity or bearing 46 which is coaxial with the clamp axis d', and open downwards, as may be seen in FIG. 7; and formation 45 is provided with a radial notch or slit 47 to make it elastically closable. A bolt 48 is inserted into a transverse bore 49 of formation 45 to secure cavity 46. Cavity 46 houses an axial extension 50 of a lower base member 51, also in the form of a half cylinder, with minimum play but with the ability to rotate about its clamp axis b', and which can also be immobilized in a preselected angular orientation by tightening bolt 48; when clamped to bone screw W", the distal diaphysis clamp will have been set to an angular orientation of distal bone screws W" with respect to the angular orientation of the proximal diaphysis bone screw W', about the axis d'. The assembly comprising axial extension 50 when inserted into cavity 46, can be immobilized by bolt 48 to form the third rotary joint of the splint. A lower cover 52 is coupled to lower base 51 by means of a bolt 20' to immobilize a second and possibly a third diaphysis screw W" in opposing seats V".

The embodiment of FIGS. 6 to 12 will be seen to enable the surgeon to insert the lower diaphysis screw into a hole provided by conventional means without any difficulty, without depending on the accuracy with which bone screws are positioned in the neck of the femur. Also, if the femoral screws have to be repositioned and their corresponding holes have to be remade, this can easily be performed in a position which is rotated with respect to the previous position, guaranteeing stability of the setting.

The third modification of FIGS. 6 to 12 relates to the nature of the quick-lock joints placed between intermediate member 4' and clamps 2', 3'. For simplicity, only one of the joints has been shown for this modification, in particular the one between member 4' and clamp 3' and governing angular adjustment about the transverse axis c'.

Figure 5:
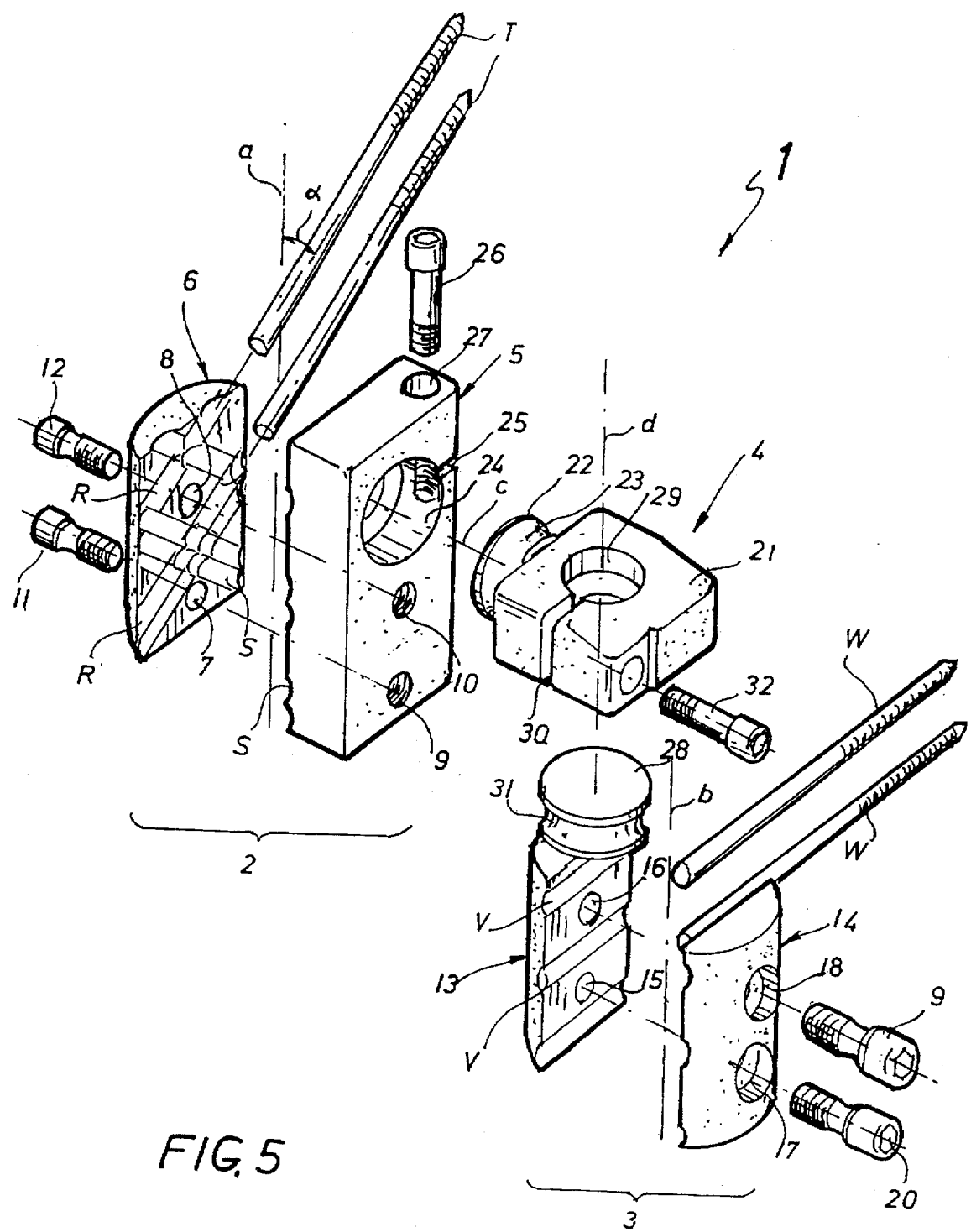
FIG. 5 is an exploded perspective view of the external splint of FIG. 1.
Figure 10:
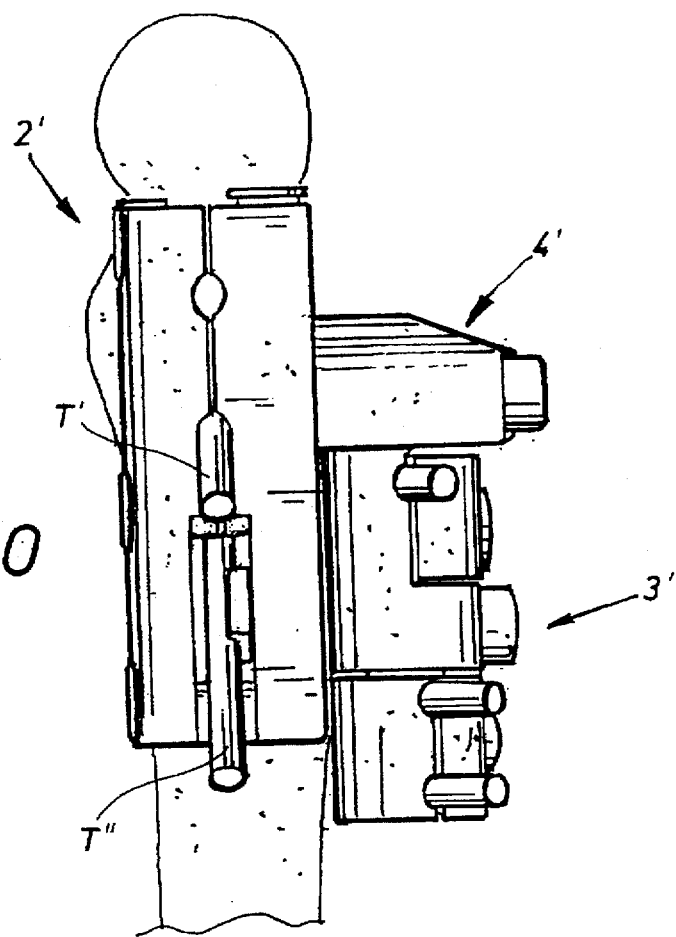
FIG. 10 is a front view of the external splint of FIG. 6.
Figure 11:
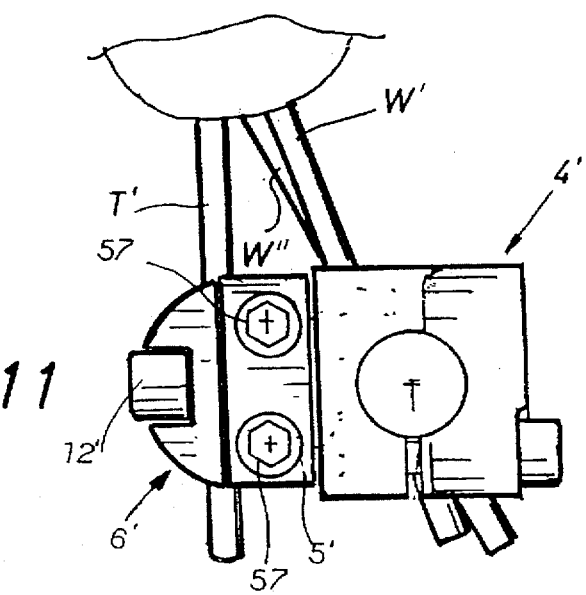
FIG. 11 is a view from above the external splint of FIG. 6.
Figure 12:
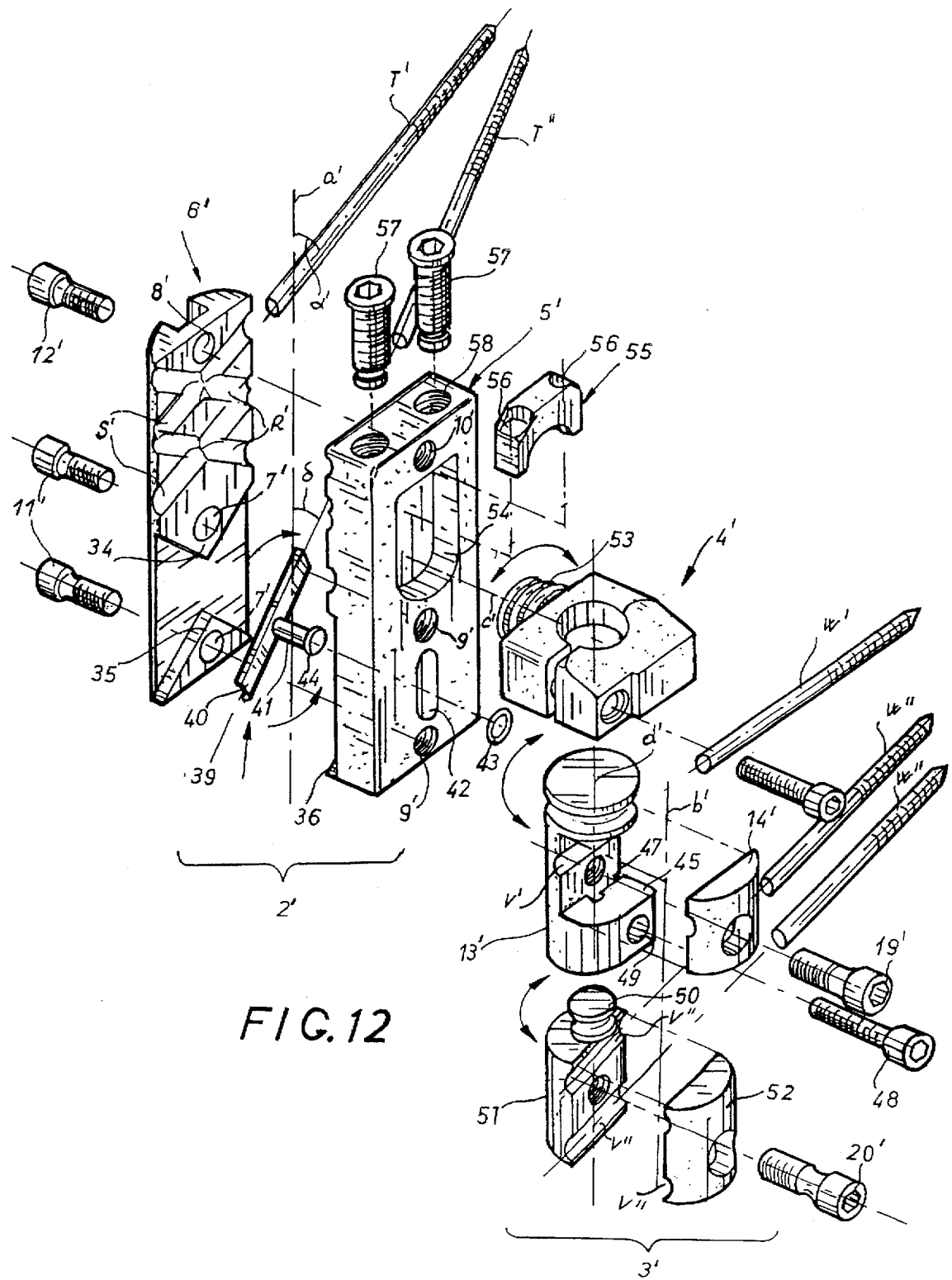
FIG. 12 is an exploded perspective view of the external splint of FIG. 6.

Instead of the substantially cylindrical axial projection 22 with a groove 23 of semicircular cross-section for passage of securing bolt 32, as illustrated in FIG. 5, a substantially cylindrical projection 53 is provided with multiple grooves having a radial cross-section in the form of a trapezium or wedge, which can clearly be seen in FIG. 7. Projection 53 is housed in the semicircular base of cavity 54 in base 5' and is held in position by an immobilizing slide 55, having a concave contact surface which is approximately semicylindrical and in a complementary shape to that of projection 53 itself, i.e. with trapezoidal grooves. On the upper part of slide 55 are two cylindrical seats 56 against which the flat ends of a pair of pressure bolts 57 act, and these in turn are threaded into corresponding threaded bores 58 formed at the upper edge of base 5'.

When bolts 57 are tightened, restraining slide 55 is pressed against projection 53. The contact surfaces of complementary shape exert a mutual wedging effect which increases the resistant torque without excessively stressing the main structure of base 5', thus increasing the security of the joint. It will be understood that this type of locking structure may also be applied in general to other rotary joints that have been described, with similar benefits in terms of security and strength.

The materials used for the members comprising clamps 2, 3, 2', 3' and for intermediate connecting member 4, 4' may be selected from those having a high strength/weight ratio, which are biologically compatible and can be sterilized in an autoclave, such as high strength aluminum alloys (UNI9007/ 2, ERGALL 55) with hard black oxidized surface treatment. The bolts may be constructed from high strength stainless steel of the type AISI 303 or AISI 304, which have been tumbled, passivated and electropolished.

It will be noted that one of covers 5, 5', 8, 8' or both of them may be joined by means of slides or elastic attachments to offer a minimum amount of longitudinal shift, in order to make the splint dynamic and encourage regeneration of the bony tissue at the focus of the fracture.

We claim:

1. An external trochanter splint, particularly for the surgical stabilization of femoral pertrochanter and subtrochanter fractures, comprising a pair of clamps (2,3) having longitudinal axes (a, b) respectively, one of the said clamps (2) being a trochanter clamp adapted to releasably secure a first group of bone screws (T) inserted into the mass of the trochanter and at least partly into the neck of the femur, the other of said clamps (3) being a femur clamp adapted to releasably secure a second group of bone screws (W) inserted into the proximal diaphysis of the femur, the said pair of clamps being coupled together in side-by-side relation by means of an intermediate connecting member (4), said intermediate connecting member establishing (i) a first fixed rotary axis of trochanter-clamp connection perpendicular to the longitudinal axis of the trochanter clamp and (ii) a second fixed rotary axis of femur-clamp connection about the longitudinal axis of the femur clamp, and selectively operable locking means for securing an adjusted rotation about each of the respective rotary axes.

2. An external splint according to claim 1, in which the said intermediate member (4) comprises a central body (21) connected to the said clamps by a pair of joints which are rotatable about their respective rotary axes (c, d), which rotary axes are substantially at right angles.

3. An external splint according to claim 2, in which each rotatable joint comprises a cylindrical seat on the one side and an extension of complementary shape rotatably housed in the said seat on the other side.

4. An external splint according to claim 3, in which the said body (21) has an internal cavity (29) defining a seat for a first rotatable joint.

5. An external splint according to claim 4, in which for the other of said rotatable joints said body (21) has an external lateral extension (22) having an axis (c) which is substantially perpendicular to the axis (d) of the seat (29) for said first rotatable joint, said external lateral extension (22) defining a pin for said other rotatable joint.

6. An external splint according to claim 1, in which each of the said clamps (2,3) comprises a base (6,7) and a cover (5, 8) having substantially flat confronting internal faces, the said base and the said cover being coupled together by means of at least one securing bolt (11, 12; 19, 20).

7. An external splint according to claim 6, in which the internal faces of the base and the cover in each clamp have at least one set of seats (R, V) to house the said groups of bone screws (T, W).

8. An external splint according to claim 7, in which the seats (V) housing the bone screws of the femur clamp (3) are substantially perpendicular to the rotary axis (b) of the said femur clamp.

9. An external splint according to claim 7, in which the seats (R) housing the bone screws of the said trochanter clamp (2) are inclined with respect to the longitudinal axis (a) of the trochanter clamp by a divergence angle ($\alpha$) which is approximately equal to the average inclination angle of the neck of the trochanter with respect to the femur.

10. An external splint according to claim 9, in which the said trochanter clamp (2) has a second set of inclined bone-screw seats (S), symmetrical to those of the first set (R) with respect to the longitudinal axis (a) of the trochanter clamp, said second set of bone-screw seats (S) being on the internal faces of the base (5) and the cover (6) of the trochanter clamp, in order to permit fitting either to a right or left limb.

11. An external splint according to claim 9, in which at least one seat for a bone screw (T") in the trochanter clamp (2') can be selectively oriented in a plane parallel to the substantially flat confronting internal faces of the trochanter clamp.

12. An external splint according to claim 11, in which the said orientable seat comprises a support (39) with a channel member (40) adapted to house a bone screw (T"), and a pivot pin (41) extending normal to the channel member, said pivot pin being received in an elongate bore (42) formed in the base (5') of the trochanter clamp so as to vary the angle of inclination ($\delta$) with respect to the axis (a') of the trochanter clamp (2').

13. An external splint according to claim 9, in which the said femur clamp comprises an upper base (13') connected to the said intermediate member (4') by said first joint, and a lower base (51) joined to the said upper base by means of a third rotary joint having an axis (b') which is coincident with that (d') of the femur clamp (3').

14. An external splint according to claim 13, in which the said third rotary joint comprises an axial extension (50) formed on the said lower base (51) and inserted into a cylindrical cavity (46) formed in an axial extension (45) of the said upper base (13'), and means including a locking bolt (48) carried by said axial extension for immobilizing an adjusted rotation of said third rotary joint.

15. An external splint according to claim 6, in which the base (13) of one of the said clamps (3) has an axial extension (28) defining a pin for the rotation of said femur-clamp connection, the said pin being capable of being inserted with a free and snug fitting into a seat (29) formed in said intermediate member (4).

16. An external splint according to claim 15, in which the base (5) of the other of the said clamps (2) has a transverse bore (24) which defines a seat for the said trochanter-clamp connection, which seat is adapted to house a cylindrical appendage (22) of the said intermediate body with a free and snug fitting.

17. An external splint according to claim 16, in which the base (5) of the clamp having said transverse bore (24) has a substantially diametral notch (25) with respect to the said bore (24) in order to make the seat of the said second joint elastically yielding.

18. An external splint according to claim 17, in which the locking means for said trochanter-clamp connection comprises a first bolt (26) tangential to the said transverse bore for selectively closing the seat (24) of the trochanter-clamp connection after the said lateral appendage (22) of the said intermediate member (4) has been oriented at will in order to adjust a divergence angle between the said clamps.

19. An external splint according to claim 18, in which the body (21) of the said intermediate member (4) has a slit (30) which is substantially radial to a central bore (29) and is capable of making the seat of the said first joint open and elastically yielding.

20. An external splint according to claim 18, in which the locking means for the femur-clamp connection comprises a second bolt (32), tangential to the seat bore (29) of the said intermediate member (4), capable of closing it off elastically to selectively lock an adjusted angle of rotation of said femur-clamp connection about its own longitudinal axis (d).

21. An external splint according to claim 16, in which the base (5') of the said trochanter clamp (2') has a cavity (54) forming a seat for the said second joint and housing an appendage (53) of the intermediate member (4') with a free and snug fitting, and in which the external surface of the said appendage (53) is substantially cylindrical with one or more grooves having a substantially trapezoidal radial cross-section.

22. An external splint according to claim 21, in which a locking block (55) is mounted adjacent the said appendage (53) and within the said cavity (54), and is secured against the same appendage by means of one or more pressure bolts (57) threaded in said base (5'), the said locking block having a concave semi-cylindrical surface which compliments that of the said appendage (53), whereby to releasably apply a locking effect on the said appendage.

23. An external bone-fixation splint, comprising first and second bone-screw clamps each having a central longitudinal axis between and parallel to inner confronting flat surfaces of a body member and of a cover member, and an intermediate member connecting said body members for selective rotary adjustment of one of said body members about a first fixed axis that is perpendicular to the inner flat surface of said one body member and for selective rotation of the other of said body members about a second fixed axis which includes the longitudinal axis of said other body member, selectively operable means for locking said rotary adjustments, and selectively operable means for clamping one or more bone screws between the inner confronting surfaces of said respective clamps.

24. An external trochanter splint according to claim 23, in which said first clamp has groove formations in one of its flat surfaces for receiving and orienting one or more trochanter screws at an acute angle to the longitudinal axis of said first clamp, and in which said second clamp has groove formations in one of its flat surfaces for receiving and orienting one or more femur bone screws substantially perpendicular to the longitudinal axis of said second clamp.

25. The splint of claim 24, in which said second clamp is a proximal diaphysis clamp and in which a third bone-screw clamp is a distal diaphysis clamp having a central longitudinal axis between parallel inner confronting surfaces of a body member and of a cover member, the body member of said third clamp having a rotary adjustment connection to the body member of said second clamp and about the central longitudinal axis of said third clamp, selectively operable means for locking an adjusted rotary orientation of said third clamp with respect to said second clamp, and selectively operable means for clamping one or more distal diaphysis bone screws to said third clamp.

26. The splint of claim 25, in which the longitudinal axes of said second and third clamps are in substantial alignment.

27. An external bone-fixation splint, comprising first and second bone-screw clamps each having a central longitudinal axis between and parallel to inner confronting flat surfaces of a body member and of a cover member, the confronting surfaces of one clamp being configured for directionally oriented clamping of at least two bone screws in a first single plane which includes the longitudinal axis of said one clamp, the confronting surfaces of the other clamp being configured for directionally oriented clamping of at least two bone screws in a second single plane which includes the longitudinal axis of the other clamp, and an intermediate member connecting said body members for selective rotary adjustment of one of said body members about a first fixed axis that is perpendicular to said first single plane and for selective rotation of the other of said body members about a second fixed axis which is parallel to the longitudinal axis of said other body member and which is perpendicular to said first fixed axis, and selectively operable means for locking said rotary adjustments.

28. An external trochanter splint, comprising trochanter clamp means and diaphysis-clamp means, each of said clamp means having a central longitudinal axis between and parallel to inner confronting flat surfaces of a body member and of a cover member, and an intermediate member connecting said body members (a) for selective rotary adjustment of the body member of said trochanter-clamp means about a first axis that is perpendicular to the inner flat surface of the body member of said trochanter-clamp means and (b) for selective rotary adjustment of the body member of said diaphysis-clamp means about the longitudinal axis of said diaphysis-clamp means, selectively operable means for locking said rotary adjustments, and selectively operable means for clamping one or more bone screws between the inner confronting surfaces of said respective clamp means.

29. An external trochanter splint according to claim 28, in which said trochanter-clamp means is adapted to releasably secure at least two spaced bone screws on convergent axes in a first plane which includes the central longitudinal axis of said trochanter-clamp means, and said diaphysis-clamp means is adapted to releasably secure at least two spaced bone screws on axes in a second plane which includes the central longitudinal axis of said trochanter-clamp means.

30. An external trochanter splint according to claim 28, in which said trochanter-clamp means has (a) first groove formations in one of its flat surfaces for receiving and orienting one or more trochanter screws in first acute-angular relation to the longitudinal axis of said trochanter-clamp means and (b) second groove formations in one of its flat surfaces for receiving and orienting one or more trochanter screws in second acute-angular relation to the longitudinal axis of said trochanter-clamp means, said first and second groove formations being in opposite directions of acute-angular relation with respect to the longitudinal axis of said trochanter-clamp means, whereby said splint is equally selectively adapted to a right-leg femur or to a left-leg femur.

31. An external trochanter splint according to claim 28, in which the respective axes of rotary adjustment intersect within said intermediate member.

\* \* \* \* \*

UNITED STATES PATENT AND TRADEMARK OFFICE
CERTIFICATE OF CORRECTION

PATENT NO. : 5,728,096
DATED : March 17, 1998
INVENTOR(S) : Giovanni FACCIOLI, et al.

It is certified that error appears in the above-indentified patent and that said Letters Patent is hereby corrected as shown below:

Column 5, line 56;  insert --define-- before "a cavity 38"

Signed and Sealed this

Tenth Day of November 1998

Attest:

BRUCE LEHMAN

*Attesting Officer*  *Commissioner of Patents and Trademarks*